United States Patent
Ostermeier et al.

(10) Patent No.: US 12,318,143 B2
(45) Date of Patent: Jun. 3, 2025

(54) IMPLANT FOR DETERMINING INTRAOCULAR PRESSURE

(71) Applicant: IMPLANDATA OPHTHALMIC PRODUCTS GMBH, Hannover (DE)

(72) Inventors: Max Ostermeier, Seevetal (DE); Stefan Meyer, Hannover (DE); Peter Szurman, Saarbrucken (DE)

(73) Assignee: IMPLANDATA OPHTHALMIC PRODUCTS GMBH, Hannover (GB)

( * ) Notice: Subject to any disclaimer, the term of this patent is extended or adjusted under 35 U.S.C. 154(b) by 0 days.

(21) Appl. No.: 17/375,711

(22) Filed: Jul. 14, 2021

(65) Prior Publication Data
US 2021/0361161 A1 Nov. 25, 2021

Related U.S. Application Data

(63) Continuation of application No. 15/319,294, filed as application No. PCT/EP2015/062976 on Jun. 10, 2015, now abandoned.

(30) Foreign Application Priority Data

Jun. 27, 2014 (DE) ...................... 10 2014 212 457.3

(51) Int. Cl.
*A61B 3/16* (2006.01)
*A61B 5/00* (2006.01)
(Continued)

(52) U.S. Cl.
CPC .............. *A61B 3/16* (2013.01); *A61B 5/0008* (2013.01); *A61B 5/0031* (2013.01); *A61B 5/01* (2013.01);
(Continued)

(58) Field of Classification Search
CPC ......... A61B 3/16; A61B 5/008; A61B 5/0031; A61B 5/01; A61B 5/6861;
(Continued)

(56) References Cited

U.S. PATENT DOCUMENTS 4,253,199 A 3/1981 Banko
4,642,114 A 4/1987 Rosa
(Continued)

FOREIGN PATENT DOCUMENTS

DE 19728069 C1 2/1999
EP 2517619 A1 10/2012
(Continued)

OTHER PUBLICATIONS

Rizq R. N. et al., "Intraocular Pressure Measurement at the Choroid Surface: a Feasibility Study with Implications for Implantable Microsystems", British Journal of Ophthalmology, BMJ Publishing Group, GB, vol. 85 No. 7, Feb. 9, 2001, p. 868-871.
(Continued)

*Primary Examiner* — Daniel L Cerioni
*Assistant Examiner* — Om Patel
(74) *Attorney, Agent, or Firm* — Notaro, Michalos & Zaccaria P.C.

(57) ABSTRACT

An implant for determining intraocular pressure includes at least one electrical pressure sensor for measuring the intraocular pressure, at least one microchip that is connected to the pressure sensor, and at least one antenna that is connected to the microchip, the microchip generating digitally encoded data from the electrical signals of the pressure sensor, which data can be transmitted by an antenna, using electromagnetic waves, to a receiver located outside the eye, and components being accommodated in a small housing, the outer dimensions of which are limited such that the implant can be positioned between the sclera and the choroid (Continued)

of the eye, is improved in that the pressure sensor is accommodated on an outer housing side of the implant, which outer housing side is brought into contact with the choroid in the eye is disclosed.

9 Claims, 2 Drawing Sheets

(51) Int. Cl.
*A61B 5/01* (2006.01)
*A61B 17/00* (2006.01)
(52) U.S. Cl.
CPC .. *A61B 5/6861* (2013.01); *A61B 2017/00893* (2013.01); *A61B 2560/0219* (2013.01); *A61B 2562/0247* (2013.01); *A61B 2562/162* (2013.01)
(58) Field of Classification Search
CPC .... A61B 2562/162; A61B 2017/00893; A61B 2560/0219; A61B 2562/0247
See application file for complete search history.

(56) References Cited

U.S. PATENT DOCUMENTS

| | | | |
|---|---|---|---|
| 5,520,631 A | 5/1996 | Nordquist | |
| 6,939,299 B1 | 9/2005 | Petersen | |
| 7,824,423 B2 | 11/2010 | Schachar | |
| 8,475,374 B2 | 7/2013 | Irazoqui | |
| 8,926,510 B2 | 1/2015 | Marshall | |
| 9,046,699 B2 | 6/2015 | Caldarise | |
| 2003/0078487 A1 | 4/2003 | Jeffries | |
| 2004/0059248 A1 | 3/2004 | Messner | |
| 2005/0064010 A1* | 3/2005 | Cooper | A61P 7/10 514/291 |
| 2005/0159660 A1* | 7/2005 | Montegrande | A61B 3/16 128/903 |
| 2009/0069648 A1* | 3/2009 | Irazoqui | A61B 5/0028 600/398 |
| 2011/0248671 A1 | 10/2011 | Dos Santos | |
| 2012/0004528 A1 | 1/2012 | Li | |
| 2012/0022505 A1* | 1/2012 | Dacquay | A61B 3/16 604/891.1 |
| 2012/0226132 A1 | 9/2012 | Wong et al. | |
| 2012/0226133 A1 | 9/2012 | Wong | |
| 2013/0150699 A1* | 6/2013 | Ostermeier | A61B 5/076 600/398 |
| 2013/0158381 A1* | 6/2013 | Rickard | A61B 3/16 604/8 |
| 2014/0200409 A1 | 7/2014 | Green | |
| 2014/0275923 A1 | 9/2014 | Haffner | |
| 2016/0302965 A1* | 10/2016 | Erickson | A61K 9/08 |

FOREIGN PATENT DOCUMENTS

| | | | | |
|---|---|---|---|---|
| JP | 2005-535392 A | 11/2005 | | |
| JP | 2013-505078 A | 2/2013 | | |
| JP | 2013-190789 A | 9/2013 | | |
| WO | 2011/035262 A1 | 3/2011 | | |
| WO | WO-2013003754 A1 * | 1/2013 | ........... | A61B 5/0031 |

OTHER PUBLICATIONS

International Search Report for PCT/EP2015/062976 filed Jun. 10, 2015.
International Search Authority Written Opinion for PCT/EP2015/02976 filed Jun. 10, 2015.

* cited by examiner

IMPLANT FOR DETERMINING INTRAOCULAR PRESSURE

CROSS REFERENCE TO RELATED APPLICATION

This is a continuation of co-pending U.S. application Ser. No. 15/319,294, filed Dec. 15, 2016, which is a 371 application of PCT/EP2015/062976, filed Jun. 10, 2015, which claims priority on German patent application no. DE 10 2014 212 457.3, filed Jun. 27, 2014, all of which are incorporated herein by reference.

BACKGROUND AND SUMMARY OF THE INVENTION

The present invention relates to an implant for determining intraocular pressure, comprising at least one electronic pressure sensor for measuring the intraocular pressure, at least one microchip that is connected to the pressure sensor, and at least one antenna that is connected to the microchip, the microchip generating digitally encoded data from the electrical signals of the pressure sensor, which data can be transmitted by the antenna, using electromagnetic waves, to a receiver located outside the eye, and said components being accommodated in a small housing, the outer dimensions of which are limited such that the implant can be positioned between the sclera and choroid of the eye.

U.S. Pat. No. 8,475,374 B2 discloses an implant of this type. This known implant comprises an artificial drainage tube or is in contact with an artificial drainage tube for watery ocular fluid in order to measure the pressure of the outflowing ocular fluid. However, an artificial drainage tube is associated with a considerable and risky intervention in the eye.

DE 197 28 069 C1 discloses an implant in which the pressure sensor is contained in an implantable intraocular lens that is inserted into the eye in place of the natural lens. This known implant is therefore not suitable for cases where the natural lens of the eye should be retained.

U.S. Pat. No. 7,824,423 B2 discloses a surgical tool for inserting implants into the eye. Moreover, this US patent discloses inserting implants into the eye that are used for scleral prosthesis and that increase the working range of the ciliary muscles in a purely mechanical manner in order to make it easier for the eye treated in this way to focus on nearby objects if the amplitude of accommodation has already declined due to age.

The object of the invention is to provide an implant for determining intraocular pressure that can be implanted into the eye with little intervention and that transmits measurement data of the highly accurately measured intraocular pressure to a receiver located outside the eye.

This object is achieved by the invention in that the pressure sensor is accommodated on the outer housing side that is brought into contact with the choroid in the eye. The implant according to the invention can be implanted into human or animal eyes in a minimally invasive manner and can remain there as a long-term implant. The implant is designed according to the invention such that it can be accommodated in a suprachoroidal cavity of the eye created for positioning the implant between the sclera and choroid, where said implant does not interfere with the functioning of the eye. Neither an artificial lens nor an artificial drainage tube for the ocular fluid is necessary. Nevertheless, the contact of the pressure sensor on the choroid ensures that the intraocular pressure is applied to the pressure sensor and can be measured accurately.

The implantation is carried out either by means of a separate implantation procedure or in combination with other ophthalmosurgical interventions such as penetrating or non-penetrating glaucoma surgery (e.g. trabeculectomy, (visco)canaloplasty or shunt implantation).

In a development of the invention it is provided for the outer housing side equipped with the pressure sensor to comprise a flexible membrane in the region of the pressure sensor as a protective layer against ingress of fluid, the intraocular pressure acting on the pressure sensor via the choroid and the membrane. The flexible membrane ensures precise transfer of the intraocular pressure, which could otherwise be distorted by housing-induced mechanical tensions if a less flexible housing material were used.

In a preferred embodiment, the implant housing is flat and elongate, preferably in the form of an ellipsoid or cuboid having rounded corners and edges. By rounding off the edges and corners, eye injuries can be prevented. In order to preserve ocular integrity, the implant must be as flat as possible, since relatively little space can be created between the sclera and the choroid. The thickness of the implant is therefore the smallest dimension thereof and should be less than 2 mm if possible.

The front face should not be too big either, in order for the scleral incision necessary for inserting the implant to be as small as possible. The width of the implant is therefore preferably less than 3.5 mm.

The largest dimension is the length of the implant, which should preferably be less than 7 mm in order to minimise the biomechanical influences on the eye as well as on the implant.

Due to its flat shape, the implant cannot rotate about its longitudinal axis within the pocket between the sclera and choroid in the eye. Only rotations about the vertical axis (see direction of rotation 32 in FIG. 3) are possible. These rotations can be performed after the implant has been inserted if it is desirable to arrange the longitudinal axis of the implant transversely to the viewing direction of the eye. The implant is normally inserted into the eye lengthways in the viewing direction of the eye by means of a scleral cut.

Usually, the implant does not rotate spontaneously in the eye. If, exceptionally, there is nonetheless a risk of rotation, the implant housing can be provided with suture loops on the outside for fixing the implant in the eye. The fastening could, for example, be designed such that closure of the implantation suture is used at the same time to fix the implant in place. For this purpose, a suture loop could be provided at the point where the implantation aperture is closed using a suture. Alternatively, an adhesion option can be provided on the implant, by means of which said implant is fixed in place as soon as the implantation aperture is closed using a biological adhesive.

In a preferred embodiment the implant housing is moulded from plastics material. In this way, the inner components such as the microchip, pressure sensor and antenna, etc. can be cast and fixed in the plastics material. Furthermore, moulding the housing from plastics material allows it to be shaped in a particularly simple manner, in particular into an ellipsoid or cuboid having rounded corners and edges.

The implant could be coated with a pharmacologically active substance, e.g. heparin, mytocin C or another substance, in order to prevent reactions such as inflammation, coagulation, tissue formation or encapsulation that would be problematic either for the eye or for pressure measurement.

In a variant, the housing can be concave on the outer housing side thereof facing the choroid, as a result of which in particular deformation of the implant or mechanical tension caused by the eye, which would distort the pressure measurement, is prevented. Embodiments having straight or convex outer housing sides are also included in the invention.

The shape of the implant side facing the inner surface of the sclera can lead to unexpected variations in the pressure measurement, e.g. as a result of cell proliferation or encapsulation reactions of the body. It is therefore proposed for the implant housing to comprise three nubs on the outer housing side thereof facing the sclera, which nubs are arranged in the manner of the corners of a triangle and are intended to come into contact with the sclera. The shape of the nubs can be round or pointed and thus form a soft "thorn" which prevents dislocation and torsion of the implant. The nubs also ensure that the implant cannot tilt and that no part of the implant other than the nubs comes into contact with the concave inner surface of the sclera. As a result, it is not necessary to adapt the outer contour of the sclera-side of the implant to different eye sizes. It has been found that the mechanical tension in the implant caused by bending can be greatly reduced by the arrangement of the nubs according to the invention.

The invention is further improved by providing the implant with an electronic temperature sensor that is connected to the microchip and is intended for measuring the temperature of the eye, the microchip generating data from the electrical signals of the temperature sensor, which data can be transmitted by the antenna, using electromagnetic waves, to a receiver located outside the eye. Specifically, scientific investigations have found that there can be steep temperature gradients inside the eye. The temperature measured in the anterior chamber or in the posterior chamber is thus different from the suprachoroidal temperature. This suprachoroidal temperature can be measured and recorded together with the hydrostatic and hydrodynamic fluid pressure in the eye using the implant according to the invention. Supplementing the pressure monitoring with temperature monitoring allows better conclusions to be drawn regarding ocular pathologies or general diseases, for example diseases of the retina or disorders of general thermoregulation of the patient.

A further embodiment of the invention provides for the antenna to consist of an electrical coil that surrounds the microchip provided with the pressure sensor. A telemetry coil of this type is particularly well suited for transmitting data to a receiver arranged outside the eye. The coil can be produced by electroplating in that a plurality of layers of the coil are electrodeposited onto a flexible or rigid, but thin, substrate.

Another embodiment consists of a thin insulated gold wire that is wound around the microchip directly or on integrated spacers. This gives the external coil arranged outside the eye a shape that allows optimal transformer coupling to the implant. The contour of the external coil can be two-dimensionally or three-dimensionally adapted to the position of the electrical coil in the implant.

The microchip in the implant can thus be designed in the manner of a RFID chip, such that the implant does not need a separate battery as a power source. The energy for transmitting the data from the implant to the external receiver is provided by means of the receiving antenna itself emitting a brief energy burst that is temporarily stored in the microchip of the implant for a short time in order to provide the energy for the subsequent transmission process.

However, the energy can also be supplied continuously throughout the measurement or data transmission process.

In an alternative embodiment, the implant can operate in the manner of an active RFID tag and carry out measurements autonomously, the results of which are saved and only transmitted to an occasionally used reader upon request. In this case, the implant requires an energy store that is charged by means of transformer coupling or energy harvesting (saccades) for example, or also by means of optical cells that are sensitive to wavelengths for which the human sclera is transparent. An autonomous system of this type would either have its own clock generator or would use the frequencies of ubiquitous GSM signals as the clock frequency. The reader could provide the trigger for a measurement via a radio link. No short-range transformer coupling is necessary for this. It is sufficient for the reader to be positioned at a distance of approximately one metre from the implant.

It is particularly expedient if the reader measures and records the external air pressure together with and at the same time as the measurement values for the intraocular pressure. A quasi-continuous recording of air pressure values can also be achieved without any contact with the implant if said implant saves the measured intraocular pressure values together with a time stamp, for example in a data logger. After the occasional reading of the data logger, the measurement values for the intraocular pressure can be assigned to the same point in time as the air pressure values measured and recorded by the reader.

BRIEF DESCRIPTION OF THE DRAWINGS

Embodiments of the invention are explained in more detail below with reference to the figures, in which, in detail.

Figure 1:
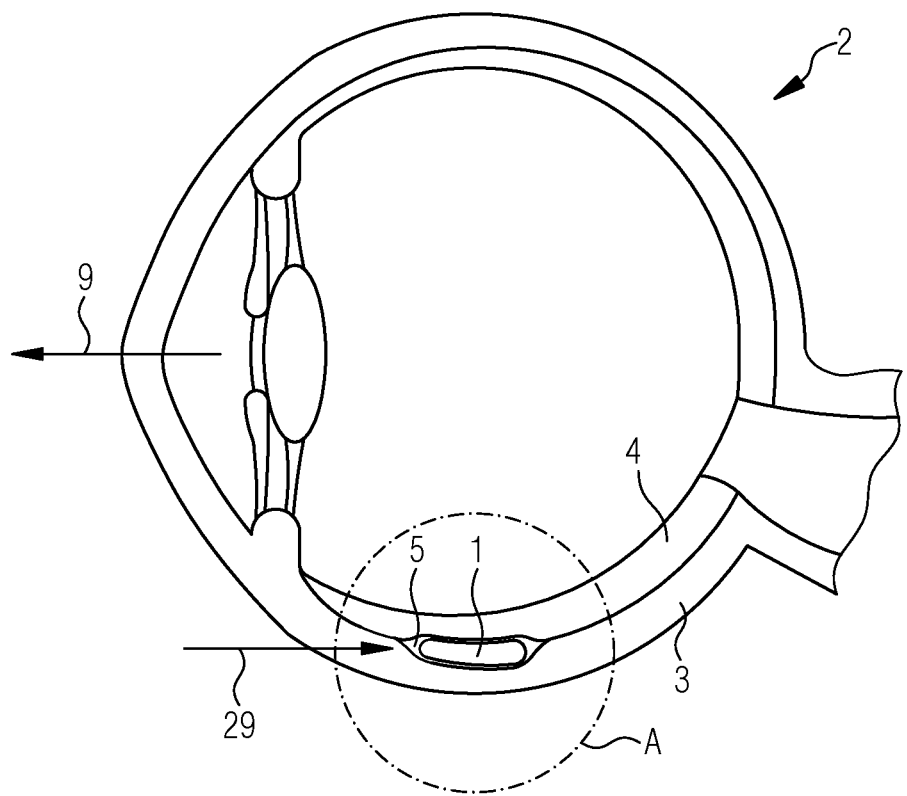
FIG. 1 is a cross section of an eye comprising an inserted implant.
Figure 2:
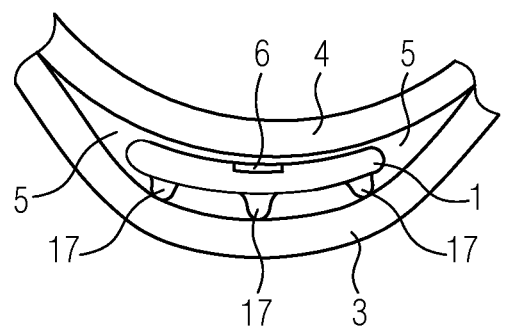
FIG. 2 is a detail A from FIG. 1 comprising the implant inserted in a pocket between the sclera and choroid.

An implant 1 according to the invention is shown in all figures and is intended to be implanted in an animal or human eye 2. The outer wall of the eye 2 is formed by the sclera 3, the inner side of which is adjacent to the choroid 4 that lies beneath it. As can be seen best in FIG. 2, the implant 1 lies in a cavity 5 that is shaped like a pocket and is formed in the suprachoroidal region between the sclera 3 and the choroid 4.

The implant 1 can be positioned ab interno transversely through the anterior chamber of the eye 2 by means of a surgical approach through the iridocorneal angle to the implantation site. Alternatively, the implant can be positioned through the sclera 3 by making the smallest incision possible, in practice approximately 5 mm long, through the sclera 3. In this way, the incision can either extend directly perpendicularly, which may require subsequent wound closure, or it can be a lamellar incision and therefore self-closing. The incision is made in the region of or behind the pars plana, for example in parallel with the ora serrata. Subsequently, a cavity or pocket 5 is formed in the suprachoroidal space between the sclera 3 and the choroid 4, using a viscoelastics material such as hyaluronic acid which is injected using an atraumatic cannula. The implant 1 can now be introduced into the pocket 5 using forceps or the insertion tool 20 described below. If required, the implant 1 is rotated inside the pocket 5 in the direction of rotation 32 by 90° about its vertical axis, which is possible due to the fact that the different layers of the eyeball merely lie on top of one another but are not stuck together.

The stability of the eye's shape is due to the intraocular pressure. Rotating the implant has the advantage of allowing the telemetry coil 8 contained in the implant to be brought into an advantageous position, as far forward as possible and directly behind the pars plana, the long side being in parallel therewith. The implant 1 is thus either in parallel with the viewing direction 9 and therefore aligned with the optical axis of the eye 2, or it is rotated by 90° relative to the viewing direction 9 and therefore oriented in parallel with the pars plana. The aim is to position the implant as far forward as possible so that it can be reached as easily as possible by the telemetry.

The surgically produced sclera aperture does not necessarily have to be closed after the implant 1 has been positioned. Normally, the sclera will grow back of its own accord without further intervention. If required, however, it can be closed by means of a suture, biological adhesive, or the like.

Figure 3:
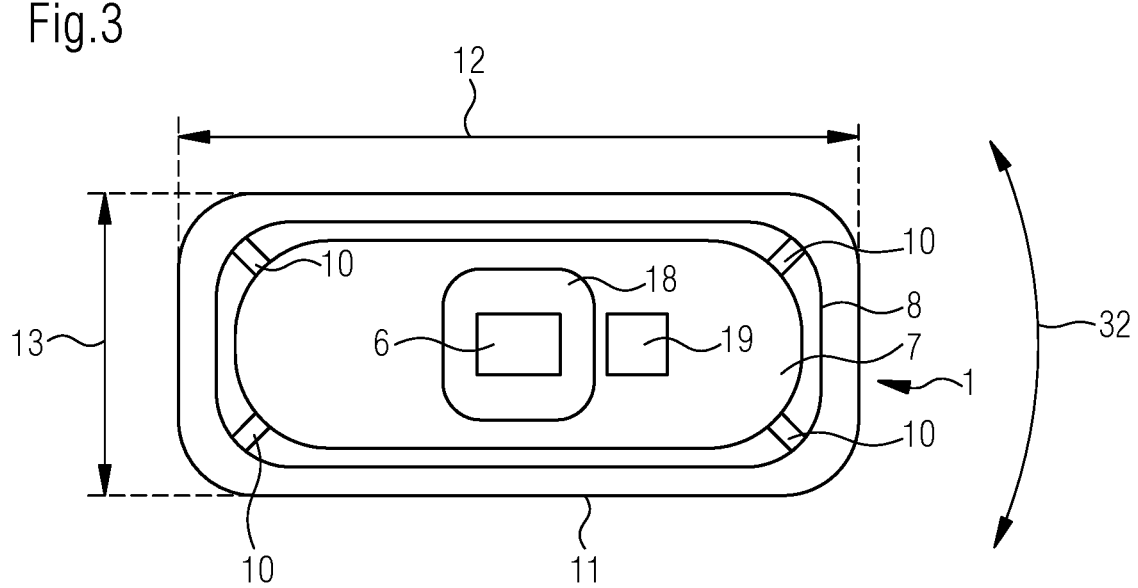
FIG. 3 is a greatly enlarged plan view of an implant according to the invention.
Figure 4:
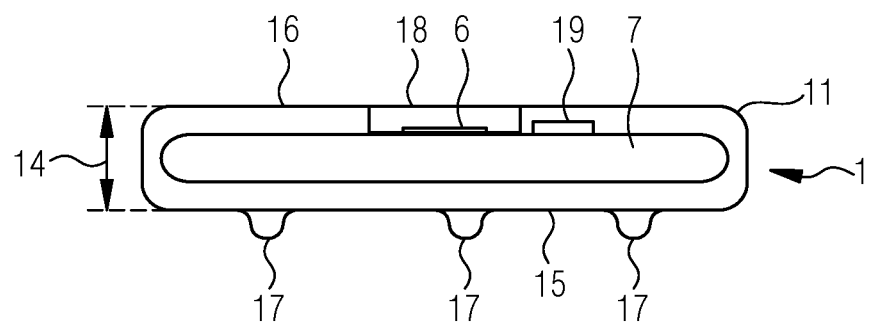
FIG. 4 is a side view of the implant from FIG. 3.

As can be seen best in FIGS. 3 and 4, the implant 1 has an electrical pressure sensor 6 for measuring the intraocular pressure, a microchip 7 on which the pressure sensor 6 is attached and connected to the microchip 7, and an antenna 8 in the form of an electrical coil that is made of insulating gold wire and supported by spacers 10. The gold wire is wound around the microchip 7 in a plurality of turns. The housing 11 of the implant 1 is moulded from synthetic resin or formed of silicone rubber, the above-mentioned components being enclosed therein. In particular, the implant could, for example, be embedded in a plurality of layers of silicone rubber having varying degrees of hardness in order to achieve greater stability. In this case, a sensor-side layer is made of softer material and a back layer is made of harder material. The housing 11 is flat and elongate and is in the shape of a cuboid having rounded corners and edges, and nubs on one housing side. The length 12 of the housing 11 is approximately 6 mm, its width 13 is approximately 3 mm and its thickness 14 is approximately 1.5 mm. The housing 11 is provided with three nubs 17 on an outer housing side 15 that faces the sclera 3 of the eye 2 in the implanted state, the nubs being arranged in the manner of the corners of a triangle. As a result, the same implant 1 can be used for eyes 2 of varying sizes, the sclera 3 of which is concavely curved to varying degrees on its inner side without the degree of curvature having a significant influence on the mechanical tension to which the implant 1 is exposed in the eye 2. As a result, the accuracy of the pressure measurement is improved.

The pressure sensor 6 is arranged on the other outer housing side 16 of the housing 11 that faces the choroid 4 in the implanted state. A flexible membrane 18 is located between the pressure sensor 6 and the choroid 4 as a protective layer against ingress of liquid. The membrane 18 presses against the pressure-sensitive surface of the pressure sensor 6 and, on the other side, against the choroid 4. The pressure sensor 6 is thus in full-surface contact with the choroid 4 via the membrane 18.

The implant 1 lies in the eye 2 in a tension-free manner between the sclera 3 and the choroid 4. Due to physiological ocular pressure and force relationships, the intraocular pressure also fixes the implant 1 in place by means of the choroid 4. The choroid 4 lies on the membrane 18 of the planarly extended pressure sensor 6 as a thin, soft choroid coat. As a result, the coupling between the pressure sensor 6 and the aqueous humour of the vitreous body of the eye 2 is not, or is only insignificantly, affected. The implant 1 therefore does not measure the pressure in the suprachoroidal space, but rather in the inner eye.

Furthermore, the implant 1 is provided with a temperature sensor 19 that is attached to the microchip 7. The temperature sensor 19 is used for measuring the temperature of the eye in the suprachoroidal space. Just like the electrical signals of the pressure sensor 6, the electrical signals of the temperature sensor 19 are registered by the microchip 7 and digital data are generated in which the temperature values and pressure values are encoded. The digital data are transmitted by the antenna 8, using electromagnetic waves, to a receiver located outside the eye 2. The pressure and temperature data can be saved in and analysed by the receiver. Analysis of the temporal progression of the pressure or temperature is thus also possible.

Figure 5:
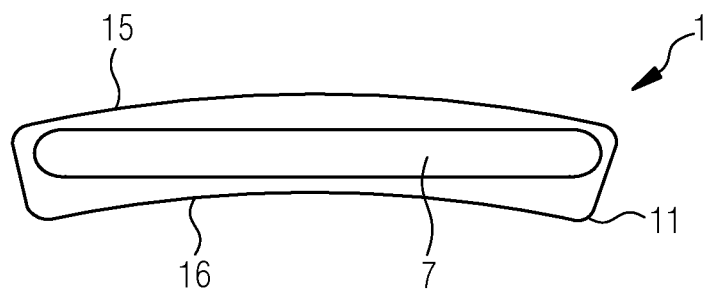
FIG. 5 is a side view of a second embodiment of the implant having concave and convex lateral faces.

In a variant, as shown in FIG. 5, the outer housing side 16 of the housing 11 of the implant 1 that faces the choroid can be concave. The outer housing side 15 of the housing 11 opposite the sclera 3 is convex in the embodiment shown. The design can take one form or the other, depending on the requirements. Thus, the convex and concave sides can also be arranged vice versa, or both sides can be convex or both sides can be concave.

LIST OF REFERENCE NUMERALS

1 Implant
2 Eye
3 Sclera
4 Choroid
5 Pocket/cavity
6 Pressure sensor
7 Microchip
8 Antenna/coil
9 Viewing direction
10 Spacer
11 Housing
12 Length
13 Width
14 Thickness
15 Outer housing side
16 Outer housing side
17 Nubs
18 Membrane
19 Temperature sensor

The invention claimed is:

1. A method for determining intraocular pressure, comprising the steps of:
   providing an implant (1), the implant comprising
   an electrical pressure sensor (6) for measuring intraocular pressure,
   a microchip (7) that is connected to the pressure sensor (6), and
   an antenna (8) that is connected to the microchip (7),
   wherein the microchip (7) generates digitally encoded data from electrical signals of the pressure sensor (6),
   wherein the digitally encoded data is transmitted by the antenna (8), using electromagnetic waves, to a receiver located outside an eye (2),
   wherein the pressure sensor (6), the microchip (7) and the antenna (8) are accommodated in and enclosed within outer walls of a housing (11) having a length

(12) less than 7 mm, a width (13) less than 3.5 mm and a thickness (14) less than 2 mm,
wherein the housing (11) comprises nubs on a first outer housing side (15) facing a concave inner surface of a sclera (3), wherein the first outer housing side (15) is formed by a first outer wall of the housing (11) and the nubs (17) protrude perpendicularly from a surface of the first outer wall which, when the implant (1) is implanted, faces the concave inner surface of the sclera (3) such that, when the implant (1) is implanted, the nubs (17) project perpendicularly from the surface of the first outer wall in a direction of the sclera (3),
wherein the housing (11) is concave on a second outer housing side (16) thereof facing a convex outer surface of a choroid (4), wherein the second outer housing side (16) is formed by a second outer wall of the housing having a concave surface without any nubs (17) which, when the implant (1) is implanted, faces and is in physical contact with the convex outer surface of the choroid (4), and
wherein the pressure sensor (6) is accommodated on the second outer housing side (16) of the implant (1);
forming a pocket (5) between the sclera (3) and the choroid (4);
positioning the implant (1) between the sclera (3) and the choroid (4) of the eye (2), and introducing the implant (1) into the pocket (5) formed between the sclera (3) and the choroid (4);
positioning the pressure sensor (6) between the sclera (3) and the choroid (4) by:
bringing the second outer housing side (16) into contact with the choroid (4) such that the pressure sensor (6) is brought into contact with the choroid (4) of the eye (2); and
positioning the first outer housing side (14) to face the sclera (3) such that the nubs (17) are brought into contact with the sclera (3).

2. The method according to claim 1, wherein the outer housing side (16) provided with the pressure sensor (6) comprises a flexible membrane (18) in the region of the pressure sensor (6) as a protective layer against ingress of liquid, the intraocular pressure acting on the pressure sensor (6) via the choroid (4) and the membrane (18).

3. The method according to claim 1, wherein the housing (11) thereof is flat and elongate in a shape of an ellipsoid or cuboid having rounded corners and edges.

4. The method according to claim 1, wherein the housing (11) is moulded from plastics material.

5. The method according to claim 1, wherein the implant (1) is provided with an electronic temperature sensor (19) that is connected to the microchip (7) and measures a temperature of the eye, and wherein the microchip (7) generates data from electrical signals of the temperature sensor (19), which data is transmitted by the antenna (8), using electromagnetic waves, to the receiver.

6. An implant, comprising:
an electrical pressure sensor (6) for measuring intraocular pressure;
a microchip (7) that is connected to the pressure sensor (6); and
an antenna (8) that is connected to the microchip (7);
wherein the microchip (7) generates digitally encoded data from electrical signals of the pressure sensor (6),
wherein the digitally encoded data is transmitted by the antenna (8), using electromagnetic waves, to a receiver located outside an eye (2),
wherein of the pressure sensor (6), the microchip (7) and the antenna (8) are accommodated in and enclosed by outer walls of a housing (11) having a length (12) less than 7 mm, a width (13) less than 3.5 mm and a thickness (14) less than 2 mm,
wherein the housing (11) comprises nubs (17) on a first outer housing side (15) facing a sclera (3), wherein the first outer housing side (15) is formed by a first outer wall of the housing (11) and the nubs (17) protrude perpendicularly from a surface of the first outer wall which, when the implant (1) is implanted, faces the concave inner surface of the sclera (3) such that, when the implant (1) is implanted, the nubs (17) project perpendicularly from the surface of the first outer wall in a direction of the sclera (3),
wherein the housing (11) is concave on a second outer housing side (16) thereof facing a choroid (4), wherein the second outer housing side (16) is formed by a second outer wall of the housing having a concave surface without any nubs (17) which, when the implant (1) is implanted, faces and is in physical contact with the convex outer surface of the choroid (4),
wherein the pressure sensor (6) is accommodated on the second outer housing side (16) of the implant (1), and
wherein the antenna (8) consists of an electrical coil that surrounds the microchip (7).

7. The implant according to claim 6, wherein the implant (1) is coated with a pharmacologically active substance, wherein the pharmacologically active substance includes one of heparin or mytocin C, in order to prevent reactions of the eye such as inflammation, coagulation, tissue formation or encapsulation that would be detrimental either to the eye or to a pressure measurement.

8. The implant according to claim 6, wherein, operating as an active radio frequency identification (RFID) tag, the implant (1) is provided with a data store in order to carry out measurements autonomously and to save a measurement data in the data store until the data are retrieved, by means of a radio link, by a reader located outside the eye (2).

9. A method of measuring intraocular pressure comprising the steps of:
providing a pressure measurement arrangement comprising an implant (1) comprising
an electrical pressure sensor (6) for measuring intraocular pressure,
a microchip (7) that is connected to the pressure sensor (6), and
an antenna (8) that is connected to the microchip (7),
wherein the microchip (7) generates digitally encoded data from electrical signals of the pressure sensor (6),
wherein the digitally encoded data is transmitted by the antenna (8), using electromagnetic waves, to a receiver located outside an eye (2),
wherein the pressure sensor (6), the microchip (7) and the antenna (8) are accommodated in and enclosed by outer walls of a housing (11) having a length (12) less than 7 mm, a width (13) less than 3.5 mm and a thickness (14) less than 2 mm,
wherein the housing (11) comprises nubs on a first outer housing side (15) facing a sclera (3), wherein the first outer housing side (15) is formed by a first outer wall of the housing (11) and the nubs (17) protrude perpendicularly from a surface of the first outer wall which, when the implant (1) is implanted, faces the concave inner surface of the sclera (3) such that, when the implant (1) is implanted, the nubs (17)

project perpendicularly from the surface of the first outer wall in a direction of the sclera (3), wherein the housing (11) is concave on a second outer housing side (16) thereof facing a choroid (4), wherein the second outer housing side (16) is formed by a second outer wall of the housing having a concave surface without any nubs (17) which, when the implant (1) is implanted, faces and is in physical contact with the convex outer surface of the choroid (4), and wherein the pressure sensor (6) is accommodated on the second outer housing side (16) of the implant (1); and providing a reader arranged outside the eye (2) for receiving measurement data that are transmitted by the implant (1) via a radio link to a receiver of the reader, wherein the reader is provided with a timer, an air pressure sensor and a data store, and provides air pressure data of the air pressure sensor with a time stamp and saves the air pressure data in the data store in order to temporally assign the saved air pressure data to the intraocular pressure measurement data delivered by the implant (1) and to correct the air pressure data, with respect to air pressure influences, to the intraocular pressure.

* * * * *